(12) United States Patent
Panesar et al.

(10) Patent No.: US 12,702,793 B2
(45) Date of Patent: Aug. 11, 2026

(54) URINARY CATHETER WITH POROUS TIP REGION

(71) Applicant: Hollister Incorporated, Libertyville, IL (US)

(72) Inventors: Satwinder S. Panesar, Foxford (IE); David J. Farrell, Ballina (IE)

(73) Assignee: Hollister Incorporated, Libertyville, IL (US)

( * ) Notice: Subject to any disclaimer, the term of this patent is extended or adjusted under 35 U.S.C. 154(b) by 271 days.

(21) Appl. No.: 18/556,631

(22) PCT Filed: Apr. 21, 2022

(86) PCT No.: PCT/US2022/025780
§ 371 (c)(1),
(2) Date: Oct. 20, 2023

(87) PCT Pub. No.: WO2022/231941
PCT Pub. Date: Nov. 3, 2022

(65) Prior Publication Data

US 2024/0198046 A1 Jun. 20, 2024

Related U.S. Application Data

(60) Provisional application No. 63/179,887, filed on Apr. 26, 2021.

(51) Int. Cl.
*A61M 25/00* (2006.01)

(52) U.S. Cl.
CPC .... *A61M 25/0068* (2013.01); *A61M 25/0017* (2013.01); *A61M 2210/1089* (2013.01)

(58) Field of Classification Search
CPC ......... A61L 29/146; A61M 2210/1078; A61M 2210/1089; A61M 25/0017; A61M 25/0068; A61M 27/00
See application file for complete search history.

(56) References Cited

U.S. PATENT DOCUMENTS

| | | | |
|---|---|---|---|
| 3,459,188 | A | 8/1969 | Roberts |
| 4,280,500 | A | 7/1981 | Ono |
| 4,698,058 | A | 10/1987 | Greenfeld |
| 5,163,924 | A | 11/1992 | Beverly |
| 5,236,422 | A | 8/1993 | Eplett, Jr. |
| 5,853,518 | A | 12/1998 | Utas |
| 5,924,206 | A | 7/1999 | Cote |
| 5,980,483 | A | 11/1999 | Dimitri |
| D421,303 | S | 2/2000 | Cote |
| D515,206 | S | 2/2006 | Tarumi |
| D515,209 | S | 2/2006 | Tarumi |

(Continued)

FOREIGN PATENT DOCUMENTS

| | | |
|---|---|---|
| CN | 3125873 | 10/1999 |
| CN | 107441570 A | 12/2017 |

(Continued)

OTHER PUBLICATIONS

International Search Report and Written Opinion mailed in connection with international application No. PCT/US2022/025780 on Aug. 26, 2022.

*Primary Examiner* — Michele Kidwell
(74) *Attorney, Agent, or Firm* — Cook Alex Ltd.

(57) ABSTRACT

A urinary catheter (10, 110) having a porous tip region (26, 22*a*, 22*b*, 22*c*, 126).

22 Claims, 2 Drawing Sheets

(56) References Cited

U.S. PATENT DOCUMENTS

| | | | | |
|---|---|---|---|---|
| D516,716 | S | 3/2006 | Weber | |
| 7,789,873 | B2 | 9/2010 | Kubalak | |
| D705,925 | S | 5/2014 | Murray | |
| 9,456,760 | B2 | 10/2016 | Hamatake | |
| 10,149,961 | B2 | 12/2018 | Carleo | |
| 10,220,185 | B2 | 3/2019 | Sadik | |
| D846,736 | S | 4/2019 | Naughton | |
| 10,307,564 | B2 | 6/2019 | Erbey, II | |
| D864,381 | S | 10/2019 | Miles | |
| 10,549,068 | B2 | 2/2020 | Shevgoor | |
| D902,387 | S | 11/2020 | Oellgaard | |
| D910,836 | S | 2/2021 | Sandberg | |
| D918,382 | S | 5/2021 | Naughton | |
| D956,222 | S | 6/2022 | Vaughan | |
| 11,376,395 | B2 | 7/2022 | Montes De Oca | |
| 2008/0262369 | A1 | 10/2008 | Colman | |
| 2012/0239004 | A1 | 9/2012 | Wong | |
| 2014/0262859 | A1* | 9/2014 | Knapp | A61M 25/0113 206/364 |
| 2015/0297862 | A1* | 10/2015 | Sadik | A61M 25/0009 604/544 |
| 2015/0352321 | A1 | 12/2015 | Hannon | |
| 2016/0367747 | A1 | 12/2016 | Loske | |
| 2017/0007800 | A1 | 1/2017 | Chao | |
| 2017/0296221 | A1 | 10/2017 | Di Caprio | |
| 2017/0348512 | A1 | 12/2017 | Orr | |
| 2018/0001055 | A1 | 1/2018 | Utas | |
| 2019/0262579 | A1 | 8/2019 | Lovmar | |
| 2020/0061335 | A1 | 2/2020 | Guldager | |
| 2020/0384241 | A1* | 12/2020 | Herrera | A61B 5/204 |
| 2020/0391005 | A1 | 12/2020 | Murray | |
| 2021/0370018 | A1 | 12/2021 | Murray | |
| 2022/0054798 | A1* | 2/2022 | Erbey | A61M 25/04 |

FOREIGN PATENT DOCUMENTS

| | | | |
|---|---|---|---|
| CN | 107670160 | A | 2/2018 |
| FR | 2240026 | A1 | 3/1975 |
| WO | 9006150 | A1 | 6/1990 |
| WO | 2011014201 | A1 | 2/2011 |
| WO | 2014077881 | A1 | 5/2014 |
| WO | 2014077886 | A1 | 5/2014 |
| WO | 2018186781 | A1 | 10/2018 |
| WO | 2020103996 | A1 | 5/2020 |
| WO | 2020160738 | A1 | 8/2020 |

* cited by examiner

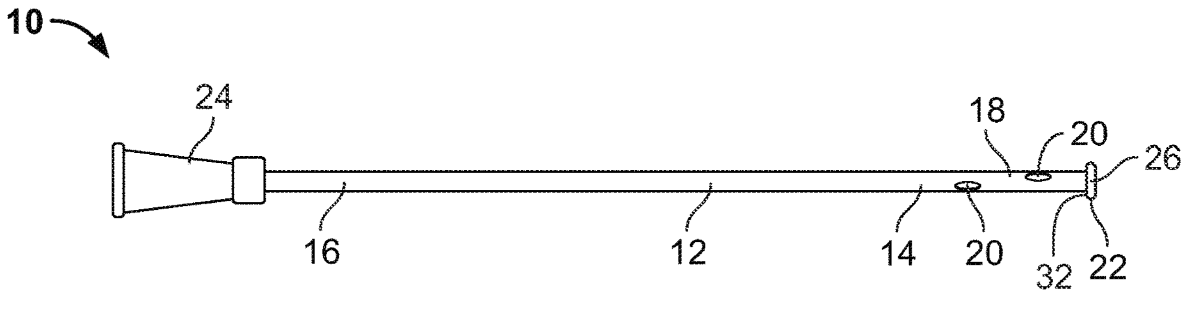
FIG. 1
FIG. 2
FIG. 3
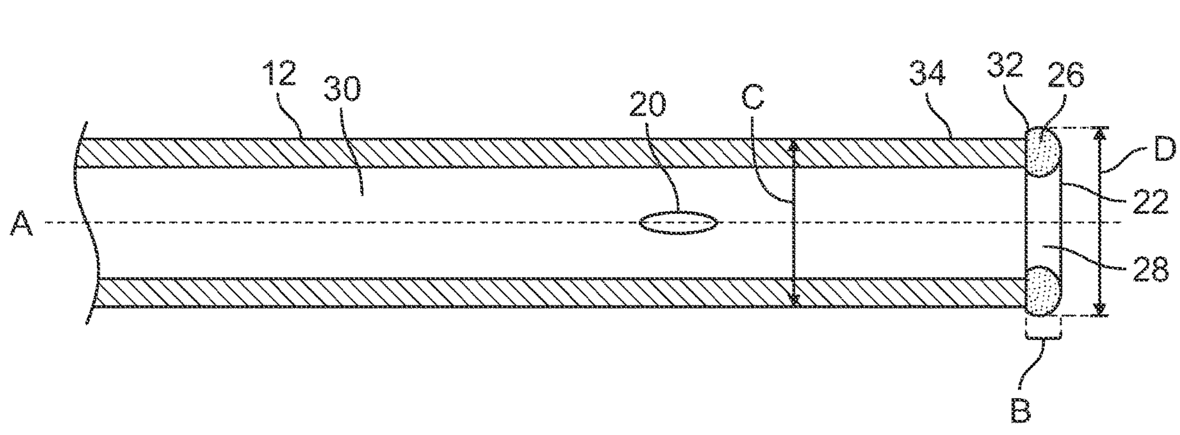
FIG. 4

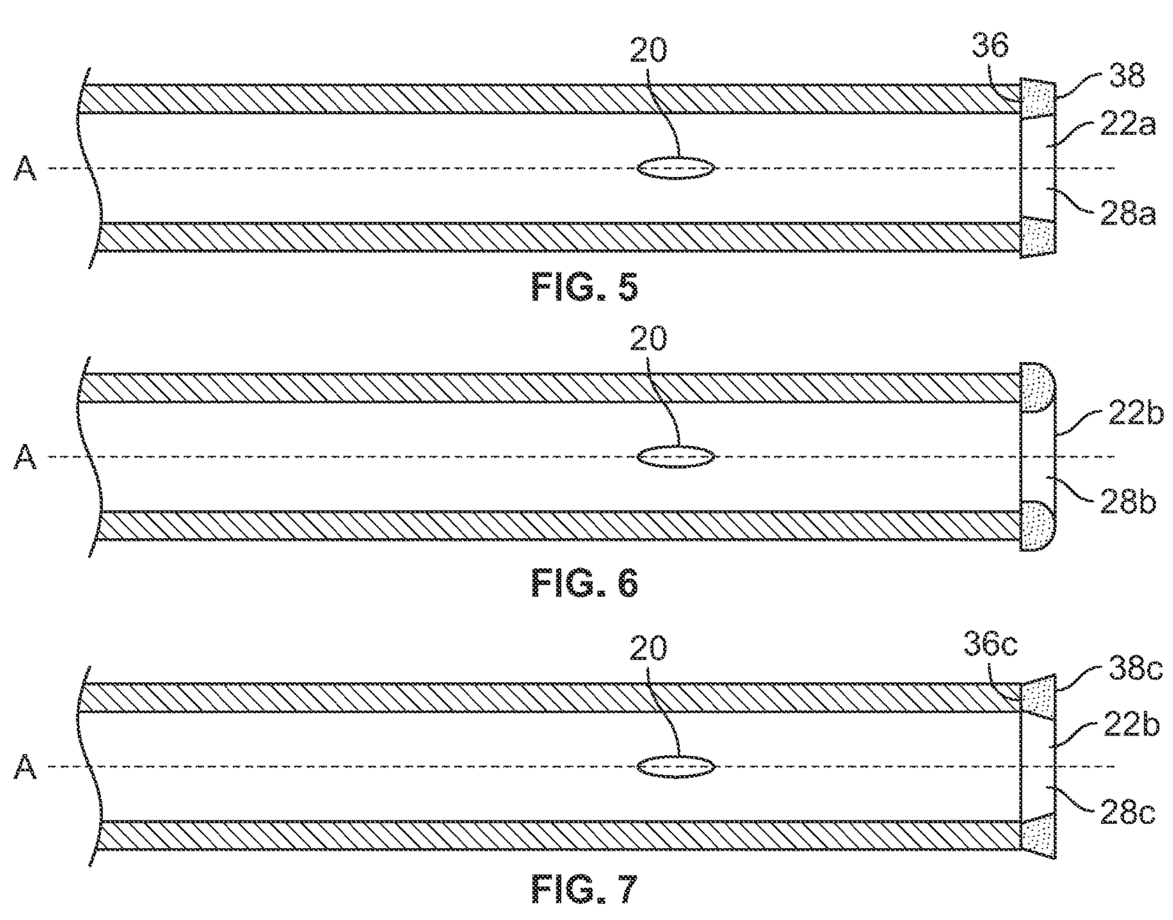
FIG. 5
FIG. 6
FIG. 7
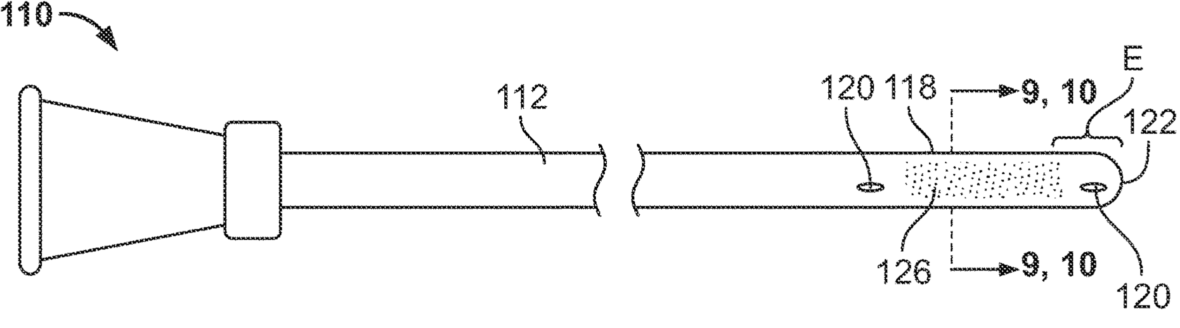
FIG. 8
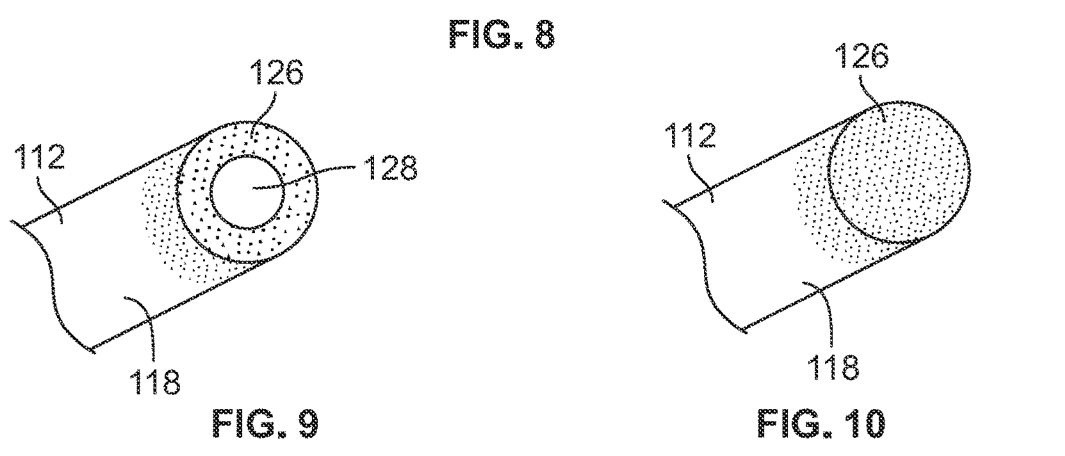
FIG. 9
FIG. 10

URINARY CATHETER WITH POROUS TIP REGION

The present application is the U.S. National Stage Application of PCT Application No. PCT/US2022/025780, filed Apr. 21, 2022, which claims the benefit of and priority to U.S. Provisional Patent Application Ser. No. 63/179,887, filed Apr. 26, 2021, the disclosure of all of which is hereby incorporated herein by reference.

FIELD OF THE DISCLOSURE

This disclosure relates generally to urinary catheters that include shafts having porous insertion end portions. More particularly, this disclosure relates to intermittent urinary catheters wherein the proximal insertion end portions of the catheter shafts include open-cell porous structures, which may be flexible, compressible, deformable and/or elastic.

BACKGROUND

Intermittent urinary catheters include a catheter shaft having a proximal insertion end portion that is inserted through the urethra and into the bladder. Once in the bladder, the urine enters the catheter through one or more discrete drainage holes or eyes that extend through the wall of the catheter shaft to the drainage lumen of the shaft. The urine enters into the drainage hole(s), drains through a drainage lumen of the catheter and is discharged out of a distal drainage opening in the distal end portion of the catheter shaft.

There remains a need for catheters with improved drainage elements.

SUMMARY

In one aspect a urinary catheter includes a catheter shaft having a proximal insertion end portion and a distal end portion. The proximal insertion end portion includes a tip region, wherein at least a section of the tip region comprises an open-cell porous structure.

BRIEF DESCRIPTION OF THE DRAWINGS

FIG. 1 is a side elevational view of one embodiment of a urinary catheter in accordance with the present disclosure;

FIG. 2 is a perspective view of the proximal insertion end portion of the catheter shown in FIG. 1;

FIG. 3 is a front end elevational view of the catheter shown in FIG. 1;

FIG. 4 is a cross-sectional view of the proximal end portion of the urinary catheter shown FIG. 1;

FIG. 5 is a cross-sectional view of the urinary catheter of FIG. 1, showing another embodiment of the terminal proximal tip;

FIG. 6 is a cross-sectional view of the urinary catheter of FIG. 1, showing another embodiment of the terminal proximal tip;

FIG. 7 is a cross-sectional view of the urinary catheter of FIG. 1, showing another embodiment of the terminal proximal tip;

FIG. 8 is a side elevational view of another embodiment of a urinary catheter in accordance with the present disclosure;

FIG. 9 is a perspective cross-sectional view of the urinary catheter taken along lines 9, 10 of FIG. 8, showing the porous region; and FIG. 10 is a perspective cross-sectional view of the urinary catheter taken along lines 9, 10 of FIG. 8, showing an alternative embodiment of the porous region.

DETAILED DESCRIPTION OF THE EMBODIMENTS

FIG. 1 illustrates one embodiment of a catheter 10 that includes an elongated catheter shaft 12 having a proximal insertion end portion 14 and a distal end portion 16. Proximal insertion end portion 14 includes a tip region 18 that is suitable for insertion into the urethra. The tip region 18, optionally, may include discrete draining holes or eyes 20 for receiving urine therethrough and into an internal conduit or drainage lumen of catheter shaft 12. Alternatively, the tip region 18 does not include discrete drainage holes or eyes that extend through the wall of the catheter shaft 12 from the outer surface to the drainage lumen of the shaft 12. The tip region 18 of proximal insertion end portion 14 includes a terminal proximal tip 22. Distal end portion 16 may include a distal opening that is in fluid communication with a drainage member 24, such as a funnel, for fluidly connecting catheter 10 to a collection container, such as a collection bag, or for directing urine to a waste receptacle, such as a toilet.

Referring to FIGS. 1-4, at least a section of the tip region 18 may be made from an open-cell porous structure 26. In the illustrated embodiment, the terminal proximal tip 22 is defined by the open-cell porous structure 26. The open-cell porous structure includes a plurality of interconnected cells or pores. In one embodiment, the open-cell porous structure 26 is made of soft or very soft, porous or spongy polymer material. Alternatively, the open-cell porous structure 26 may be relatively stiff. The open-cell porous structure 26 may also be deformable, compressible, viscoelastic and/or elastic. In one embodiment, the open-cell porous structure 26 may have a shore hardness of less than 30 shore. For example, the shore hardness may be between about 15 shore and about 30 shore, or less than 15 shore.

Additionally, several of the pores or cells of the open-cell porous structure 26 are interconnected, which allows for drainage of urine from the bladder through the open-cell porous structure 26 into the drainage lumen of the catheter tube. The open-cell porous structure 26 may also have an infinity to soak up liquids, such as urine or antimicrobial solutions. The size and number of pores can be selected to have a desired urine flow therethrough and to allow urine flow to continue even in the event that some of the pores become blocked. In one alternative, pores of the open-cell porous structure 26 may have a size between about 10 um and about 100 um. In some alternative embodiments, interconnected pores may a variety of sizes up to 1000 um. This provides for optionally allowing the catheter shaft 12 to not have discrete relatively large eyelets/drainage holes that extend through the wall of the catheter tube from the outer surface to the drainage lumen.

The open-cell porous structure 26 may have a sponge-like structure. The open-cell porous structure may be made from a foamed polymer. In an alternative, the structure 26 may be made from sintered polymer particles. Additionally, the open-cell porous structure 26 may be reticulated. The open-celled porous structure may also have a density of less than $0.2/cm^3$. The open-cell porous structure may be made from polyurethane, PTFE, PVA, PE, graphene, silicones etc. and/or composites of polymers, and hydrophilic polymers.

The open-cell porous structure 26 may also have low frictional interfacial properties. Additionally, the open-cell porous structure can have hydrophilic or hydrophobic characteristics. Such characteristics may be an integral part of the material of the porous structure or may be imparted by a coating applied to the structure. In the embodiment of applying a coating to the porous structure 26, blockage of the porous by the coating is avoided by applying a positive pressure from inside of the porous structure 26 during the coating process and, optionally, during any subsequent cure/drying process. For example, when the catheter shaft 12 includes a lubricous hydrophilic coating, during the process of coating the catheter shaft 12, a positive pressure can be applied from inside the catheter lumen or the porous structure 26 to prevent the hydrophilic coating from blocking the pores. In one embodiment, the porous structure 26 has a coefficient of friction of less than or equal to 0.01.

The porous structure 26, optionally, can be coated or impregnated with anti-microbial materials e.g., anti-microbial metals (Silver, Copper) or biocompatible metals (ex. AgO or $TiO_2$), encapsulated or impregnated citric acid, hypochlorous acid, Hydrogen peroxide, quaternary ammonium compound etc.

Referring back to FIGS. 1-4, the terminal proximal tip 22 defined by the porous structure 26 can be in an integral part of the catheter shaft 12 or can be attached to the catheter shaft 12 by any suitable joining method, such as glue, melting, spin welding, etc. In the illustrated embodiment, the terminal tip 22 defined by the porous structure 26 has a generally torus, toroidal, ring or doughnut shape. In this embodiment, the terminal tip 22 has a central hole or orifice 28 that that is in communication with the drainage lumen 30 (FIG. 4) of the catheter shaft 12. The central hole 28 may be coaxial with the drainage lumen 30 of the catheter shaft 12. The central hole 28 is sufficient to allow efficient urine drainage from the bladder into the drainage lumen 30 of the catheter shaft 12. In one embodiment, the central hole 28 may have a dimension, such as a diameter, that is greater than or equal to about 1 mm. In another embodiment the dimension of the central hole 28 may be greater than or equal to about 2 mm. Furthermore, the axial length "B" of the terminal proximal tip 22 defined by the structure may be between 1 mm and 40 mm.

Referring to FIG. 4, the terminal proximal tip 22 of the catheter shaft 12 has a dimension "D" in a plane perpendicular to the longitudinal axis "A" of the catheter shaft 12 that is large than a diameter "C" of a remaining portion of the catheter shaft 12. In other words, the terminal proximal tip 22 of the catheter shaft 12 has a cross-sectional dimension in a plane perpendicular to the longitudinal axis "A" of the catheter shaft 12 that is larger than a diameter of a remaining portion of the catheter shaft. Alternatively, or in addition to, the terminal proximal tip 22 of the catheter shaft 12 has a portion or lip 32 that extends in a radial direction beyond an outer surface 34 of an immediately adjacent distal segment of the catheter shaft 12. The flexibility and/or low coefficient of friction of the porous structure 26 of the terminal proximal tip 22 assists in allowing the tip to easily guide through varying urethra surface obstacles.

FIGS. 5-7 illustrate different embodiments of ring-shaped terminal proximal tips 22*a*-22*c* made from an open-cell porous structure. Each of these tips 22*a*-22*c* have a central opening 28*a*-28*c* for draining urine. FIG. 5 illustrates a terminal proximal tip 22*a* defined by the open-celled porous structure that has a cross-sectional profile in a plane parallel to the longitudinal axis "A" of the catheter shaft 12, wherein the cross-sectional profile has a polygonal shape. In the illustrated embodiment, the polygonal shape of the cross-sectional profile is trapezoidal. Furthermore, the terminal proximal tip 22*a* includes a base 36 and a top 38, wherein the base is adjoined to the catheter shaft 12. The widest dimension of the base 36 in a radial direction is wider than the widest dimension of the top 38 in a radial direction. Turning to FIG. 6, the terminal proximal tip 22*b* defined by the open-celled porous structure has a cross-sectional profile in a plane parallel to the longitudinal axis "A" of the catheter shaft 12, wherein cross-sectional profile has a stilted arch shape. In FIG. 7, the cross-sectional profile of the terminal proximal tip 22*c* is trapezoidal, wherein the widest dimension of the top 38*c* in a radial direction is wider than the widest dimension of the base 36*c* in a radial direction.

FIGS. 8-10 illustrate other embodiments of catheters 110 in accordance with the present disclosure. In these embodiments, a section 114 of the tip region 118 of the catheter shaft 112 comprises an open-celled porous structure/region 126 having the same characteristics and features as described above with respect to open-celled porous structure 26. The open-celled porous structure 126 is in fluid communication with the drainage lumen of the catheter shaft 112. In some embodiments, the tip region 118 includes an open terminal proximal tip 122. Alternatively, the terminal proximal tip 122 may be closed. The open-celled porous structure 126 may extend distally from the terminal proximal tip 122. In an alternative, the open-celled porous structure 126 may be spaced a distance "E" of about 1 mm to about 40 mm from the terminal proximal tip 122.

The opened celled porous structure 126 has a length perpendicular to the longitudinal axis of the catheter shaft 112, wherein the length is between about 3 mm and about 5 mm. The opened celled porous structure 126 may extend circumferentially around the catheter shaft 112. In other embodiments, the opened celled porous structure 126 may include interrupted section that are spaced about the catheter shaft 112. As shown in FIG. 9, the open-celled porous structure 126 may have a central hole 128 that is in communication with the drainage lumen of the catheter shaft 112. The central hole 128 may be coaxial with the drainage lumen and may have a larger or smaller diameter than the drainage lumen. Alternatively, the open-cell porous structure 126 may be a continuous structure spanning or covering the drainage lumen, as shown in FIG. 10.

The catheter 110, optionally may include discrete drainage eyes 120 extending through the wall of the catheter shaft 112, wherein in the eyes 120 are in a proximal and/or distal location from the open-celled porous structure 126.

It should be understood that various changes and modifications to the presently preferred embodiments described herein will be apparent to those skilled in the art. Such changes and modification can be made without departing from the spirit and scope of the invention disclosed herein.

What is claimed is:

1. A urinary catheter, comprising:

a catheter shaft having a proximal insertion end portion, a distal end portion, and a drainage lumen; and the proximal insertion end portion including a tip region, wherein at least a section of the tip region comprises an open-cell porous structure having interconnected pores that extend from an outer surface of the tip region to an inner surface of the tip region and that are in fluid communication with the drainage lumen, such that urine drains from a bladder through the open-cell porous structure and into the drainage lumen.

2. The urinary catheter of claim 1, wherein the open-cell porous structure defines a terminal proximal tip of the catheter shaft.

3. The urinary catheter of claim 2, wherein the terminal proximal tip defined by the open-cell porous structure includes a central opening that is coaxial and in fluid communication with the drainage lumen of the catheter shaft.

4. The urinary catheter of claim 2, wherein the terminal proximal tip defined by the open-cell porous structure has a generally torus or toroidal shape.

5. The urinary catheter of claim 2, wherein the terminal proximal tip defined by the open-cell porous structure has a cross-sectional profile in a plane parallel to a longitudinal axis of the catheter shaft, wherein the cross-sectional profile has a polygonal shape.

6. The urinary catheter of claim 5, wherein the polygonal shape of the cross-sectional profile is trapezoidal.

7. The urinary catheter of claim 2, wherein the terminal proximal tip includes a base and a top, wherein a widest dimension of the base is wider than a widest dimension of the top.

8. The urinary catheter of claim 2, wherein the terminal proximal tip includes a base and a top, wherein a widest dimension of the top is wider than a widest dimension of the base.

9. The urinary catheter of claim 2, wherein the terminal proximal tip defined by the open-cell porous structure has a cross-sectional profile in a plane parallel to a longitudinal axis of the catheter shaft, wherein cross-sectional profile has a stilted arch shape.

10. The urinary catheter of claim 2, wherein the terminal proximal tip of the catheter shaft has a cross-sectional dimension in a plane perpendicular to a longitudinal axis of the catheter shaft that is larger than a diameter of a remaining portion of the catheter shaft.

11. The urinary catheter of claim 2, wherein the terminal proximal tip of the catheter shaft has a portion that extends in a radial direction beyond an outer surface of an immediately adjacent segment of the catheter shaft.

12. The urinary catheter of claim 1, wherein the tip region includes a terminal proximal tip.

13. The urinary catheter of claim 12, wherein the terminal proximal tip is closed.

14. The urinary catheter of claim 12, wherein the open-cell porous structure extends distally from the terminal proximal tip.

15. The urinary catheter of claim 12, wherein the open-cell porous structure is spaced about 1 mm to about 40 mm from the terminal proximal tip.

16. The urinary catheter of claim 1, wherein the open-cell porous structure has a length perpendicular to a longitudinal axis of the catheter shaft, wherein the length is between about 3 mm and about 5 mm.

17. The urinary catheter of claim 1, wherein in the open-cell porous structure extends circumferentially around the catheter shaft.

18. The urinary catheter of claim 1, wherein the proximal insertion end portion does not include discrete drainage eyes that extend through a wall of the catheter shaft.

19. The urinary catheter of claim 1, wherein the open-cell porous structure comprises a foamed polymer.

20. The urinary catheter of claim 1, wherein the open-cell porous structure comprises a sintered polymer particles.

21. The urinary catheter of claim 1, wherein the open-cell porous structure comprising cells having a size between 10 um and 100 um.

22. The urinary catheter of claim 1, wherein the open-cell porous structure is deformable, compressible and/or flexible.

* * * * *